United States Patent [19]

Ritter

[11] Patent Number: 4,515,724

[45] Date of Patent: May 7, 1985

[54] BORON ALKYL COMPOUNDS AND PROCESSES FOR THEIR MANUFACTURE AND USE

[75] Inventor: Wolfgang Ritter, Düsseldorf, Fed. Rep. of Germany

[73] Assignee: Henkel Kommanditgesellschaft auf Aktien, Düsseldorf, Fed. Rep. of Germany

[21] Appl. No.: 412,518

[22] Filed: Aug. 30, 1982

[30] Foreign Application Priority Data

Mar. 1, 1982 [DE] Fed. Rep. of Germany ....... 3207264

[51] Int. Cl.$^3$ ............................ C09F 5/08; C09F 7/10; C11C 3/00

[52] U.S. Cl. ................................ 260/410; 260/410.6; 260/410.9 R; 260/410.9 N

[58] Field of Search ......... 260/410 R, 410.6, 410.9 R, 260/410.9 M, 410.9 N; 568/1, 7

[56] References Cited

U.S. PATENT DOCUMENTS

| | | | |
|---|---|---|---|
| 2,925,437 | 2/1960 | Brown | 568/1 |
| 2,925,438 | 2/1960 | Brown | 568/1 |
| 2,985,633 | 5/1961 | Welch | 260/85.3 |
| 3,078,311 | 2/1963 | Brown | 568/1 |
| 3,078,313 | 2/1963 | Brown | 568/1 |
| 3,085,112 | 4/1963 | Brown | 568/7 |
| 3,150,157 | 9/1964 | Liao | 260/410 R |
| 3,476,727 | 11/1969 | Lo Monaco et al. | 260/92.8 |
| 3,633,490 | 1/1972 | Schiffmann et al. | 99/339 |
| 4,167,616 | 9/1979 | Bollinger | 526/197 |

FOREIGN PATENT DOCUMENTS

| | | |
|---|---|---|
| 2321215 | 11/1973 | Fed. Rep. of Germany . |
| 1113722 | 5/1968 | United Kingdom . |

OTHER PUBLICATIONS

Brown et al., JACS 86, 1791–1807(1964).

*Primary Examiner*—Helen M. S. Sneed
*Attorney, Agent, or Firm*—Ernest G. Szoke; Mark A. Greenfield; Henry E. Millson, Jr.

[57] ABSTRACT

Novel boron alkyl compounds which are esters of a fatty acid or a fatty alcohol and which have at least one boryl radical or organoboron radical attached thereto. These boron alkyl compounds can be used to harden monomer adhesives, and are stable and active even when exposed to air.

30 Claims, No Drawings

BORON ALKYL COMPOUNDS AND PROCESSES FOR THEIR MANUFACTURE AND USE

BACKGROUND OF THE INVENTION

Boron alkyl compounds are known to be capable of initiating free radical polymerizations at room temperature in the presence of oxygen or compounds that supply oxygen. Oxygen needed for initiating polymerization is always present, and need not be added separately. Simple trialkyl boron compounds such as triethyl boron or tri-n-butyl boron have been proposed for this purpose. The use of trialkyl boron compounds as polymerization initiators has been disclsed, for instance, in U.S. Pat. Nos. 3,476,727; 3,633,490; and 2,985,633 as well as British Pat. No. 1,113,722. U.S. Pat. No. 4,167,616 discloses reaction products of butadiene and diborane, and their application as polymerization initiators.

Such boron alkyl compounds are also suitable as reaction initiators or as hardeners for reactive adhesives which contain systems based on polymerizable monomers. Methacrylate adhesives in particular are examples of such systems. In addition to acrylic acid esters or methacrylic acid esters, these adhesives contain trialkyl boron compounds, such as triethyl boron or tri-n-butyl boron, as their essential component (see Japanese Application No. 42/14,318 (1967). Such trialkyl boron compounds, however, have the disadvantage that they are readily flammable, which makes handling of such adhesives quite difficult.

Attempts have been made to overcome this disadvantage by reacting the trialkyl boron compounds with 0.3 to 0.9 mole of oxygen; see German Application No. 23 21 215. Attempts have also been made to react the trialkyl boron compounds with amines in order to reduce their spontaneous ignition properties; see Japanese Application No. 45/29,195 (1970).

By the use of these techniques the ignition temperature is shifted into the range of 0° to 70° C.; however, considerable uncertainty remains with respect to the handling of such mixtures. In addition, the reactivity of these boron alkyl derivatives is greatly reduced.

If unlimited quantities of oxygen come into contact with free boron alkyls, oxidation to boric acid esters occurs, with attendant loss of their ability to be used as polymerization initiators. Until now, in order to preserve the activity of boron alkyl compounds as initiators, it was necessary to eliminate all contact with oxygen when using or measuring them, and of course also during their manufacture. Consequently, any required quantity of the boron alkyl material must be packaged by means of an inert gas into totally air tight vessels in order to eliminate the possibility of oxygen entering the storage vessel. The portioned boron alkyls must then be used quantitatively. Due to these complications, the previously described systems are not suitable for a number of applications; for example, they are unsuited for many practical uses of adhesives.

Boron alkyl initiators show substantial advantages over conventional initiators of free radical polymerizations such as the peroxides, hydroperoxides, or azo-compounds. For example, polymerizations initiated by boron alkyls can be carried out at low temperatures. Also, the starter system/hardener system is available in a single component form. Furthermore, the rate of polymerization can be influenced by varying the amount of oxygen available.

The described disadvantages of simple trialkyl boron compounds, and in particular, their spontaneous ignition liabilities may be partially eliminated by the careful selection of more stable boron alkyl compounds. An example thereof is 9-borabicyclo[3.3.1]nonane (9-BBN). However, this dialkyl boron hydride, as well as other more stable boron alkyls, dissolves with great difficulty, or very slowly, in many monomers, especially monomer systems containing ester groups. This places a serious limitation on the use of these known boron alkyl compounds that are more stable when exposed to atmospheric oxygen.

DETAILED DESCRIPTION OF THE INVENTION

The present invention has as its object the manufacture of boron alkyl compounds with all of the above mentioned advantages of boron alkyl initiators, especially when added to monomers or monomer containing systems, and which will initiate easily controllable polymerizations while being oxidized by atmospheric oxygen, but which will not exhibit spontaneous ignition even when in pure form. In addition, the boron alkyl initiators must dissolve easily and quickly in monomer systems, in particular, in monomers containing ester groups, in order to render them suitable for the polymerizing or hardening of methacrylic acid ester systems.

This invention, therefore, in one of its first embodiments relates to new boron alkyl compounds with improved stability when exposed to atmospheric oxygen, and good solubility in reactive adhesives that are based on monomers containing polymerizable double bonds. The new boron alkyl compounds of the invention are characterized in that they contain boron hydride radicals or organoboron radicals on fatty acid esters and/or on fatty alcohol esters. Further embodiments of the invention relate to the manufacture of these new boron alkyl compounds, and their use as polymerization initiators, in particular for reactive adhesive systems.

The new boron alkyl compounds of the invention are hydroborated addition products of diborane and/or an organoboron compound with at least one B-H bond, to a fatty acid ester and/or to a fatty alcohol ester having, in at least one portion of the fatty acid radical and/or fatty alcohol radical, a carbon-carbon double bond addition site. The new boron alkyl compounds are particularly suited for hardening monomer adhesives, for example those based on methacrylate. In contrast to traditional boron alkyl hardeners, they offer definite advantages, including the following:

(a) the boron alkyl compounds of the invention do not, under normal conditions, ignite spontaneously, and are comparatively easy to store;
(b) the amount of hardener needed to harden the monomer components is exceedingly small;
(c) hardeners within the scope of this invention remain fully active even after prolonged storage in air; and
(d) the compatability of monomer system and hardener component can be controlled by proper selection of the ester component which also acts as the carrier matrix.

With respect to the composition and the manufacture of the new boron alkyl compounds, the following criteria are applicable.

Esters or ester mixtures to be used as the matrix contain, via a B—C bond, boron hydride radicals and/or organoboron radicals as substituents. Insofar as these boron containing substituents are not the boryl radical —$BH_2$ itself, these boron containing substituents, in a further preferred embodiment, have bonded to the boron, with at least one additional B—C bond, one or more organic radicals. Preferred organic radicals are hydrocarbon radicals which may also contain heteroatoms, in particular O, N and/or S. Suitable organic radicals include alkyl, cycloalkyl, and/or aryl radicals which can be present on one or both boron valences that are not utilized by the ester matrix. If such organic radicals other than hydrogen are present on both remaining boron valences, they can form their own ring system.

The boron compounds of the invention that can be used as polymerization initiators can be obtained by hydroborating the ester matrix starting material containing the olefinic double bonds with diborane or preferably with a mono-substituted borane, or more preferably, with a disubstituted borane. Such substituted boranes have the general formula $R_1R_2BH$, wherein $R_1$ is an organic radical, preferably a hydrocarbon radical, and $R_2$ is hydrogen or an organic radical, which can be identical to or different from $R_1$, or can form a ring system with $R_1$ and the boron atom. Preferred hydrocarbon radicals are alkyl, cycloalkyl, and/or aryl radicals. Hydrocarbon radicals as substituents on the boron preferably contain not more than 25 carbon atoms, and preferably not more than about 15 carbon atoms. In a special and preferred embodiment, $R_1$ and $R_2$ together with the boron atom form a ring system containing no more than the above number of carbon atoms.

An especially suitable group of organoboron compounds to be used for the manufacture of the polymeric initiator components are the organoboron monohydride compounds, in particular dialkylmonohydrides. Typical representatives of such boron compounds are, for example, 9-borabicyclo[3.3.1]nonane (9-BBN), diisopinocampheylborane, dicyclohexylborane, thexylborane(2,3-dimethyl-2-butylborane), 3,5-dimethylborinane, and diisoamylborane. Of the above compounds, the first mentioned 9-BBN is preferred for practical reasons. The above compounds can be manufactured, for example, from sodium boron hydride and boron trifluoride with suitable olefins or diolefins. Diborane, its ether complex, amine complex, or sulfide complex can also be used in the process for their preparation. A compilation of methods for the manufacture of suitable boron compounds can be found in a monograph by Herbert C. Brown, 1975 "Organic Syntheses via Boranes", published by John Wiley & Sons.

The ester base which serves as a matrix in accordance with this invention has important significance. The starting material for this matrix is characterized in that monofunctional fatty acids and/or monofunctional fatty alcohols are converted into esters or ester mixtures, having at least in one part of their fatty acid constituent and/or fatty alcohol constituent a receptive hydrocarbon double bond available for addition. For ease of reference, these constituents may be referred to hereinafter as unsaturated components.

The term fatty acid or fatty alcohol includes monofunctional components of the type referred to above with a number of carbons in the range of about 8 to about 32 carbon atoms, preferably about 12 to about 22 carbon atoms. The unsaturated fatty acids or the unsaturated fatty alcohols can be of synthetic or natural origin. Preferred are mono- or polyolefinically unsaturated alkene monocarboxylic acids or monoalkenols with the number of carbons given above. The carbon chains of these fatty acids or fatty alcohols can be straight chain or branched chain.

The complementary component forming the individual ester can be a monofunctional or polyfunctional alcohol or a monofunctional or polyfunctional carboxylic acid. It is possible to have the carbon-carbon double bonds which are receptive to addition in only one constituent, i.e. only in the fatty acid or the fatty alcohol; however, both ester forming components can contain olefinic double bonds. In the manufacture of the boron alkyl compounds of the invention, at least a substantial number of these double bonds will be hydroborated.

In a preferred embodiment of this invention, the ester matrix is formed through esterification of a monofunctional component (acid or alcohol) with a polyfunctional complementary component (alcohol or acid). Especially suitable matrix materials are esters of unsaturated monocarboxylic acids (unsaturated fatty acids) with polyhydroxy alcohols. Reaction components that form polyhydroxy esters are corresponding compounds with a functionality up to 6, preferably with a functionality of 2 to 4. In the preferred embodiment of the invention, as matrix for the boron containing substituents, monocarboxylic acids of the stated carbon atoms are esterified with polyhydroxy alcohols, especially with dihydroxy, trihydroxy, or tetrahydroxy alcohols.

It can therefore be advantageous to have polyfunctional ester components that have an equally small number of carbon atoms, for example, in the 2 to 10 range, preferably between 2 and 6 carbon atoms. As polyfunctional alcohols there can be used the lower glycols such as ethylene glycol, 1,2-propylene glycol, 1,3-propylene glycol, the $C_4$-glycols with terminal and/or inner hydroxyl groups or the corresponding $C_5$- and $C_6$-compounds. Especially preferred alcohols include glycerin (glycerol) and polyhydroxy alcohols of the pentaerythritol type. Conversely, monofunctional fatty alcohols with a lower polycarboxylic acid, especially a lower dicarboxylic acid or lower tricarboxylic acid can be used herein for esterification. The terms "lower polycarboxylic acid", "lower dicarboxylic acid" and "lower tricarboxylic acid" are understood to mean such acids having from 2 to 6 carbon atoms in addition to the carbon atoms in the carboxyl groups.

The use of synthetic or natural fats and/or oils as the ester matrix for subsequent hydroboration falls within the scope of this invention. The unsaturated esters or mixtures thereof can be present in admixture with saturated components, for example, in an admixture with saturated esters.

Esters used herein, including fats and/or oils, with ethylenic double bonds available for hydroboration can range from low viscosity and flowable up to solids, depending on their structure and molecular weight. For certain applications, such as in the area of reaction adhesives, it is desirable to use the organoboron compounds that have low viscosity or are at least viscous and flowable or spreadable at room temperature. However, this is not a prerequisite for the effectiveness of the organoboron compounds that are used as initiators. On the contrary, the storage stability of organoboron compounds that are solids at room temperature is particularly good.

The unsaturated esters or ester mixtures such as fats, oils, and the like can be ethylenically unsaturated to any extent prior to hydroboration. Preferred are starting materials that have an iodine number up to about 280, preferably in the range of about 1 to about 205, and more preferably from about 5 to about 130.

Especially suitable are, for example, the following fats or oils of natural origin:

| Name | Iodine Number |
| --- | --- |
| Coconut oil | 7.5–10.5 |
| Palm kernel oil | 14–23 |
| Beef tallow | 40–48 |
| Palm oil | 44–54 |
| Lard | 55–57 |
| Sperm oil | 70 |
| Castor oil | 81–91 |
| Peanut oil | 84–100 |
| Rapeseed oil | 97–108 |
| Cottonseed oil | 99–103 |
| Soybean oil | 120–141 |
| Herring oil | 123–142 |
| Sunflower oil | 126–136 |
| Linseed oil | 155–205 |

Esters or ester mixtures obtained from the following fatty acids are the preferred starting materials for the ester matrix in accordance with this invention:

| Description | Common Name | Double Bonds |
| --- | --- | --- |
| dodecenoic acid | Lauroleic acid | 1 |
| tetradecenoic acid | Myristoleic acid | 1 |
| hexadecenoic acid | Palmitoleic acid | 1 |
| octadecenoic acid | Oleic acid | 1 |
| eicosenoic acid | Gadoleic acid | 1 |
| docosenoic acid | Erucic acid | 1 |
| 12-hydroxy-octadecenoic acid | Ricinoleic acid | 1 |
| octadecadienoic acid | Linoleic acid | 2 |
| octadecatrienoic acid | Linolenic acid | 3 |
| eicosatetraenoic acid | Arachidonic acid | 4 |
| docosapentaenoic acid | Clupanodonic acid | 5 |

As addition receptors for hydroboration, esters of unsaturated fatty alcohols can be used with saturated or even unsaturated mono- or dicarboxylic acids, for example, the ethyl acetate of oleyl alcohol, the glycolic acid diester of oleyl alcohol, and the adipic acid ester of oleyl alcohol, as well as similar compounds.

The extent of hydroboration of the ester matrix can be selected anywhere within the scope of the availability of the double bonds. However, it was found to be advantageous if at least a substantial portion of these double bonds are reacted by introducing the boron containing substituents. In the preferred embodiments of this invention, more than 30%, preferably between about 50% and 100%, and more preferably between about 70% and 100% of the originally present ethylenic double bonds in the ester matrix are hydroborated. Particularly suitable are organoboron compounds where, in relation to the reaction starter formulation, at least 80%, preferably at least 90%, or even 95% of the ethylenic double bonds are reacted with the boron containing components.

For hydroboration purposes, the unsaturated esters are reacted in the complete absence of oxygen with the selected boron hydride compounds. It is therefore expedient to work with solvents. Suitable are the known solvents for organoboron compounds, in particular tetrahydrofuran, glycol, or polyethers such as diethyleneglycol dimethylether, but also esters, hydrogen halides, and the like. The reaction is usually carried out in the temperature range of about 0° to about 100° C., preferably in the range between room temperature and about 70° C.

The hydroborated ester products can then be isolated by distilling off the solvent. Depending on the composition and molecular weight, such products can be viscous to solid. A sealed vessel is suggested for storage, preferably under an inert gas such as nitrogen. However, these boron alkyl compounds are relatively stable in air. Selected components can, for example, be left exposed to air in an open dish for an entire day, and still exhibit starter properties for hardening olefinic components which are comparable to those of the freshly prepared corresponding boron containing compounds or to those that had been stored without contact with oxygen.

When using the new boron alkyl compounds as starters for polymerizable substances, in particular for reaction adhesives, the boron initiators are added in amounts of about 0.1 to about 40 wt. %, preferably about 0.1 to about 30 wt. % in relation to the weight of the material to be polymerized. It is especially advantageous to add the hardener of the invention in amounts of about 0.5 to about 10 wt. % in relation to the weight of the material to be polymerized. As polymerizable ingredients, numerous known compounds with polymerizable ethylenic double bonds can be used for different applications such as bonding metal, wood, glass, ceramics, and/or synthetic materials.

Concerning the relationship between structure and reactivity, the following can be stated:

1. Hydroboration products of unsaturated esters, such as oils or fats or their corresponding mixtures, with alkyl boranes, such as the 9-BBN type, are more active as polymerization initiators than the corresponding reaction products with boron hydride. The above mentioned boron alkyl ester derivatives are also far less sensitive to atmospheric oxygen.
2. In order to obtain simultaneously high reactivity and optimum nonsensitivity to atmospheric oxygen, total hydroboration of the olefinic groups in the matrix is desirable.
3. Hydroboration products of fatty acid esters of monofunctional components (monofunctional acids, and monofunctional alcohols) are far less stable in air than the corresponding ester derivatives in which polyfunctional reaction components were used. Therefore, the 9-BBN hydroboration products of fatty acid esters of monofunctional alcohols, such as lower alkanols, are far less stable in air than comparable derivatives which were manufactured using glycerine or pentaerythrite as the alcohol component.
4. The hydroboration products of fats with a high iodine number are more active than the corresponding derivatives of products with a low iodine number.

Hydroboration products of fatty acid esters of monofunctional alcohols and polyfunctional alcohols exhibit matching activity at comparable iodine numbers.

Organoboron compounds of the invention used herein have so far not been isolated or investigated. The literature cites occasional references to their intermediate formation within the scope of extensive reactions. See J. Am. Chem. Soc. 92, 2467, 1970.

The invention is illustrated by the following examples, which are not given for purposes of limitation.

EXAMPLES

(a) Manufacture of 9-BBN derivatives of fats, oils, or fatty acid derivatives In order to remove residual oxygen, fats, oils, or fatty acid derivatives were dissolved in an equal quantity of degassed tetrahydrofuran (THF). Afterwards, the solvent was distilled off in a $10^{-4}$ Torr vacuum. Using a glove box, once again the same quantity by weight of freshly distilled, degassed THF was added, and the fats, oils, or fatty acid derivatives were dissolved therein. Under complete absence of oxygen, the amounts of 9-borabicyclo[3.3.1]nonane (9-BBN) given in Table 1 were added, and the mixture was continuously stirred until the 9-BBN dissolved quantitatively. Heating was carried out for 1 hour with stirring at 60° C. The THF was distilled off in a vacuum, and the storage vessel sealed. The removal of samples must be carried out under a protective gas and with complete absence of oxygen.

TABLE 1

Reaction of oils, fats, and fatty acid derivatives with 9-BBN

| Example No. | Oil, Fat Fatty Acid Derivative | Iodine Number | Amount of 9-BBN/g used per 100 g of material | Degree of modification of the double bonds % | Product Properties |
| --- | --- | --- | --- | --- | --- |
| 1 | Palm oil Solid | 51.9 | 24.9 | 100 | Viscous, orange color |
| 2 | Palm oil, Liquid | 64.4 | 30.5 | 100 | Homogeneous, viscous, orange color |
| 3 | Oleic acid methyl ester | 85.8 | 41 | 100 | Homogeneous, slightly viscous, yellow |
| 4 | Peanut oil | 92 | 43 | 100 | Homogeneous, viscous, yellow |
| 5 | Edenor MESj* | 125 | 60 | 100 | Homogeneous, slightly viscous, colorless |
| 6 | Linseed oil | 178 | 86 | 100 | Homogeneous, viscous, light yellow |
| 7 | Peanut oil | 92 | 13 | 30 | Homogeneous, slightly viscous, light yellow |
| 8 | Edenor MESj* | 125 | 18 | 30 | Homogeneous, slightly viscous, colorless |
| 9 | Soybean oil | 130 | 18.5 | 30 | Homogeneous, viscous, brown |
| 10 | 1,2-propylene glycol dioleate | 93 | 43.5 | 100 | Homogeneous, slightly viscous, lighty yellow |
| 11 | Pentaerythrite-tetraoleate | 93 | 43.5 | 100 | Homogeneous, slightly viscous, light yellow |
| 12 | Jojoba oil (synthetic) | 89 | 41.7 | 100 | Homogeneous, slightly viscous, dark yellow |

*$C_{18}' \cdot C_{18}''$ - Fatty acid methylester mixture of Henkel KGaA.

The reaction process was observed using $^{1}$H-NMR-spectrum (—C$\underline{H}$=CH— resonance at $\delta = 5.3$ ppm) and $^{13}$C-NMR-spectrum (—CH=CH— resonance at $\delta = 129.5$ and 129.8 ppm). The conversion of the double bonds for Example 3 was 70±5%.

(b) Manufacture of BH$_3$-derivatives of fats, oils, or fatty acid derivatives To remove the residual oxygen, the fats, oils or fatty acid derivatives were dissolved in equal quantities of THF. Afterwards, the solvent was distilled off in a $10^{-4}$ Torr vacuum. Using a nitrogen current at a constant temperature of 5° C., 0.33 mole of diborane/THF per double bond was added dropwise to the fatty derivative. The reaction was exothermic. The reaction mixture was heated to room temperature, and subsequently stirred for an additional hour at 60° C. The THF solution was filtered under nitrogen, the THF distilled off in a high vacuum, and the storage vessel sealed. Removal of samples was accomplished under a protective gas and in the complete absence of oxygen. Details of these examples are given in Table 2.

TABLE 2

Reaction of oils, fats, and fatty acid derivatives with BH$_3$

| No. | Oil, Fat, Fatty Acid Derivative | Iodine Number | Degree of modification of the double bonds % | Product Properties |
| --- | --- | --- | --- | --- |
| 13 | Peanut oil | 92 | 100 | Viscous, clear |
| 14 | Edenor MESj | 125 | 100 | Slightly viscous, colorless |

(c) Application of the described fat based boron alkyls as hardeners for monomeric adhesives General Procedure:

40 g of polymethacrylic acid methyl ester (PMMA commercially availabe powder)* were dissolved in 45 g of methacrylic acid methyl ester (MMA), and 5 g of methacrylic acid in a beaker while stirring. To each 5 g of this solution between about 1.5 and 23 wt. % of a boron alkyl starter described in (a) and (b) above (see Tables 1 and 2) were added with vigorous stirring. The pot life of the mixtures varied between 1 and 15 minutes. These adhesives were used within the pot life to bond sand blasted and degreased sheet iron and after 24 hours the bonding strength was determined in a stress shearing test in accordance with German Industrial Standard (DIN) 53 281/3. The results are given in Table 3.

*Plexigum MB319, Röhm Co., Darmstadt.

To prove the high stability of the described fatty acid based boron alkyls when exposed to atmospheric oxygen, another test series was performed in which they were exposed to air in open containers between 24 and 72 hours, and were then used as hardeners and tested. Their pot life and stress shearing strengths are listed in parentheses in Table 3.

TABLE 3

Pot times and shearing strength for sandblasted and degreased test samples of sheet iron when hardening methacrylate adhesives (40 g PMMA, 45 g MMA, 5 g MAA) with the boron alkyls given in Tables 1 and 2.

The results of the measurements in parenthesis are for boron alkyl hardeners that had been stored in air for the stated time periods at room temperature prior to application.

| Hardener Concentration Wt % | Pot Life Min. | | Stress Shearing Strength $Nmm^{-2}$ | |
|---|---|---|---|---|
| Boron alkyl from Example 1 | | | | |
| 1.5 | 11 | | 3 | |
| 3 | 9 | | 4 | |
| 5 | 8 | | 6 | |
| 10 | 5 | | 8 | |
| 23 | 3 | | 3 | |

After being stored in air for 24 hours, this boron alkyl is no longer active.

| Boron alkyl from Example 2 | | | | |
|---|---|---|---|---|
| 1.5 | 10 | (14) | 14 | (0) |
| 3 | 7.5 | (10) | 21 | (7) |
| 5 | 6.5 | (6.5) | 20 | (14) |
| 10 | 5 | (6) | 16 | (14) |
| 23 | 2 | (2) | 10 | (13) |

The results of the measurements in parenthesis are for the boron alkyl hardener after storage in air at room temperature for 24 hours prior to use.

| Boron alkyl from Example 3 | | |
|---|---|---|
| 1.5 | 10 | 17 |
| 3 | 6 | 27 |
| 5 | 3.5 | 28 |
| 10 | 3 | 28 |

After being stored in air for 24 hours, this boron alkyl is no longer active.

| Boron alkyl from Example 4 | | | | |
|---|---|---|---|---|
| 1.5 | 6 | | 23 | |
| 3 | 4.5 | (6.5) | 25 | (20) |
| 5 | 3.5 | (5) | 22 | (20) |
| 10 | 3 | (3) | 17 | (14) |
| 23 | 1.5 | (1) | 17 | (11) |

The results of the measurements in parenthesis are for the boron alkyl hardener after storage in air for 48 hours at room temperature prior to use.

| Boron alkyl from Example 5 | | |
|---|---|---|
| 1.5 | 5 | 16 |
| 3 | 5 | 24 |
| 5 | 5 | 17 |
| 10 | 6 | 7 |
| 23 | 7.5 | 4 |

After being stored in air for 24 hours, this boron alkyl is no longer active.

| Boron alkyl from Example 6 | | | | |
|---|---|---|---|---|
| 1.5 | 3 | (4) | 28 | (28) |
| 3 | 3 | (3) | 28 | (28) |
| 5 | 2.5 | (2.5) | 23 | (24) |
| 10 | 1.5 | (2.5) | 15 | (18) |
| 23 | 1 | (1) | 14 | (11) |

The results of the measurements in parenthesis are for the boron alkyl hardener after storage in air for 24 hours prior to use.

| Boron alkyl from Example 7 | | |
|---|---|---|
| 1.5 | 13 | 0 |
| 3 | 7 | 0 |
| 5 | 4 | 1 |
| 10 | 2.5 | 2 |
| 23 | 2 | 3 |

After being stored in air for 24 hours, this boron alkyl is no longer active.

Boron alkyls from Examples 8 and 9.
These boron alkyls exhibited no activity.

| Boron alkyl from Example 10 | | | | |
|---|---|---|---|---|
| 1.5 | 6 | (8) | 26 | (10) |
| 3 | 5.5 | (5.5) | 26 | (21) |
| 5 | 5 | (5) | 25 | (17) |
| 10 | 3 | (3) | 20 | (18) |
| 23 | 1 | (2) | 14 | (11) |

The values in parenthesis are for the boron alkyl hardener after storage in air at room temperature for 72 hours prior to use.

| Boron alkyl from Example 11 | | | | |
|---|---|---|---|---|
| 1.5 | 5 | (9) | 26 | (17) |
| 3 | 5 | (7.5) | 26 | (20) |

TABLE 3-continued

Pot times and shearing strength for sandblasted and degreased test samples of sheet iron when hardening methacrylate adhesives (40 g PMMA, 45 g MMA, 5 g MAA) with the boron alkyls given in Tables 1 and 2.

The results of the measurements in parenthesis are for boron alkyl hardeners that had been stored in air for the stated time periods at room temperature prior to application.

| Hardener Concentration Wt % | Pot Life Min. | | Stress Shearing Strength $Nmm^{-2}$ | |
|---|---|---|---|---|
| 5 | 4 | (5.5) | 23 | (19) |
| 10 | 3.5 | (4) | 19 | (15) |
| 23 | 0.5 | (2) | 13 | (11) |

The values in parenthesis are for the boron alkyl hardener after storage in air for 72 hours at room temperature prior to use.

| Boron alkyl from Example 12 | | | | |
|---|---|---|---|---|
| 1.5 | 6.5 | (7.5) | 20 | (16) |
| 3 | 5.5 | (6.5) | 26 | (20) |
| 5 | 5 | (5.5) | 24 | (17) |
| 10 | 2.5 | (3.5) | 21 | (16) |
| 23 | 1 | (2) | 18 | (11) |

The values in parenthesis are for the boron alkyl hardener after storage in air for 72 hours at room temperature prior to use.

| Boron alkyl from Example 13 | | |
|---|---|---|
| 1.5 | 15 | 7 |
| 3 | 6 | 6 |
| 5 | 2 | 9 |
| 10 | 1.5 | 6 |
| 23 | 1 | 1 |

After being stored in air for 24 hours, this boron alkyl is no longer active.

| Boron alkyl from Example 14 | | |
|---|---|---|
| 1.5 | 15 | 17 |
| 3 | 2 | 11 |
| 5 | 2 | 8 |
| 10 | 2 | 7 |
| 23 | 1 | 1 |

After being stored in air for 24 hours, this boron alkyl is no longer active.

What is claimed is:

1. A boron alkyl compound comprising the addition product of an unsaturated ester, having double bonds of which about 30 to 100% are hydroborated with a boron compound;

said ester being either (a) comprised within at least one naturally occurring unsaturated fat or oil or mixture thereof having about 12 to 22 carbon atoms, or (b) at least one synthetic reaction product of a $C_{12-22}$ hydroxy or non-hydroxy fatty acid or alcohol which has at least one olefinic double bond with a complementary polyfunctional alcohol or carboxylic acid containing from 2 to 10 carbon atoms in addition to any carboxyl radicals present; and said ester (a) or (b) having an iodine number between about 5 and 130;

said boron compound being at least one borane or organoborane having at least one alkyl, cycloalkyl or aryl radical with from 1 to 25 carbon atoms;

and wherein said boron alkyl compound has enhanced stability in the presence of air and is soluble in reaction systems containing monomers having polymerizable double bonds.

2. The boron alkyl compound of claim 1 wherein said ester is comprised within the at least one naturally occurring unsaturated fat or oil.

3. The boron alkyl compound of claim 2 wherein said ester is comprised within: coconut oil, palm kernel oil, beef tallow, palm oil, lard, sperm oil, castor oil, peanut oil, rapeseed oil, cottonseed oil, soybean oil, herring oil, sunflower oil, linseed oil, or mixtures thereof.

4. The boron alkyl compound of claim 1, 2, or 3 wherein said boron compound is the organoborane.

5. The boron alkyl compound of claim 4 wherein said organoborane radicals have from 1 to 15 carbon atoms.

6. The boron alkyl compound of claim 4 wherein said at least one radical and the boron atom form a ring system.

7. The boron alkyl compound of claim 4 wherein said organoborane compound is: 9-borabicyclo[3.3.1]nonane; diisopinocampheylborane; dicyclohexylborane; 2,3-dimethyl-2-butylborane; 3,5-dimethylborinane; or diisoamylborane.

8. The boron alkyl compound of claim 4 wherein said organoborane compound is 9-borabicyclo[3.3.1]nonane.

9. The boron alkyl compound of claim 1, 2, or 3 wherein said boron compound is a.$BH_3$.

10. The boron alkyl compound of claim 1 wherein said ester is the at least one synthetic reaction product of a $C_{12-22}$ hydroxy or non-hydroxy fatty acid or alcohol which has at least one olefinic double bond with a complementary polyfunctional alcohol or carboxylic acid containing from 2 to 10 carbon atoms in addition to any carboxyl radicals present.

11. The boron alkyl compound of claim 10 wherein said fatty acid or alcohol has from 14 to 22 carbon atoms.

12. The boron alkyl compound of claim 10 wherein said fatty acid or alcohol is dodecenoic, tetradecenoic, hexadecenoic, octadecenoic, eicosenoic, docosenoic, 12-hydroxy-octadecenoic, octadecadienoic, octadecatrienoic, eicosatetraenoic, or docasapentaenoic acid or alcohol or mixtures thereof.

13. The boron alkyl compound of claim 10, 11, or 12 wherein said polyfunctional compound is a polyfunctional alcohol having from 2 to 6 hydroxyl radicals, a polyfunctional acid having from 2 to 6 carboxyl radicals, or mixtures thereof.

14. The boron alkyl compound of claim 13 wherein said polyfunctional compound has 2 to 6 carbon atoms in addition to any carboxyl radicals present.

15. The boron alkyl compound of claim 10, 11, or 12 wherein said polyfunctional compound is a lower glycol, a $C_4$ glycol with terminal and/or inner hydroxyl groups, the corresponding $C_5$ or $C_6$ glycols, the corresponding glycollic acids, or mixtures thereof.

16. The boron alkyl compound of claim 15 wherein the polyfunctional compound is glycerol or pentaerythritol.

17. The boron alkyl compound of claim 14 wherein said organoborane compound is a .$BH_3$.

18. The boron alkyl compound of claim 14 wherein said boron compound is an organoborane and wherein said organoborane radicals have from 1 to 15 carbon atoms.

19. The boron alkyl compound of claim 18 wherein said organoborane compound is: 9-borabicyclo[3.3.1]nonane; diisopinocampheylborane; dicyclohexylborane; 2,3-dimethyl-2-butylborane; 3,5-dimethylborinane; or diisoamylborane.

20. The boron alkyl compound of claim 18 wherein said organoborane compound is 9-borabicyclo[3.3.1]nonane.

21. The boron alkyl compound of claim 1 wherein said ester is (a) and at least one of: solid palm oil, liquid palm oil, oleic acid methyl ester, peanut oil, a $C_{18'}$-$C_{18''}$ fatty acid methylester mixture, linseed oil, peanut oil, soybean oil, 1,3-propylene glycoldioleate, pentaerythritetraoleate, or synthetic jojoba oil.

22. The boron alkyl compound of claim 21 wherein said boron compound is 9-borabicyclo[3.3.1]nonane.

23. The boron alkyl compound of claim 22 wherein the degree of hydroboration of the double bonds is about 100%.

24. The boron alkyl compound of claim 1 wherein said ester is at least one of peanut oil or a $C_{18'}$-$C_{18''}$ fatty acid methylester mixture, wherein said boron compound is .$BH_3$, and wherein the degree of hydroboration of the double bonds is about 100%.

25. The boron alkyl compound of claim 1 wherein the degree of hydroboration of the double bonds is about 50 to 100%.

26. The boron alkyl compound of claim 1 wherein the degree of hydroboration of the double bonds is about 70 to 100%.

27. The boron alkyl compound of claim 4 wherein the degree of hydroboration of the double bonds is at least 80%.

28. The boron alkyl compound of claim 4 wherein the degree of hydroboration of the double bonds is at least 90%.

29. The boron alkyl compound of claim 18 wherein the degree of hydroboration of the double bonds is at least 80%.

30. The boron alkyl compound of claim 18 wherein the degree of hydroboration of the double bonds is at least 90%.

* * * * *